(12) United States Patent
Kim

(10) Patent No.: US 11,241,303 B2
(45) Date of Patent: Feb. 8, 2022

(54) APPARATUS FOR INSERTING MEDICAL TUBE AND SURGICAL PROCEDURE KIT FOR INSERTING MEDICAL TUBE, HAVING SAME

(71) Applicant: Y.JACOBS MEDICAL INC., Seoul (KR)

(72) Inventor: Young Jae Kim, Seoul (KR)

(73) Assignee: Y.JACOBS MEDICAL INC., Seoul (KR)

( * ) Notice: Subject to any disclaimer, the term of this patent is extended or adjusted under 35 U.S.C. 154(b) by 350 days.

(21) Appl. No.: 16/298,406

(22) Filed: Mar. 11, 2019

(65) Prior Publication Data

US 2019/0201178 A1 Jul. 4, 2019

Related U.S. Application Data

(63) Continuation of application No. 15/102,240, filed as application No. PCT/KR2013/011310 on Dec. 6, 2013, now Pat. No. 10,226,320.

(51) Int. Cl.
*A61F 2/00* (2006.01)
*A61B 17/34* (2006.01)
(Continued)

(52) U.S. Cl.
CPC ........ *A61F 2/0059* (2013.01); *A61B 17/3468* (2013.01); *A61B 2017/00792* (2013.01);
(Continued)

(58) Field of Classification Search
CPC ...... A61B 2017/00792; A61B 17/3468; A61B 17/0482; A61B 2017/06176; A61B 2017/06185; A61F 2/0059
See application file for complete search history.

(56) References Cited

U.S. PATENT DOCUMENTS 3,123,077 A 3/1964 Alcamo
3,981,307 A 9/1976 Borysko
(Continued)

FOREIGN PATENT DOCUMENTS

CN 101219066 A 7/2008
CN 2012166619 Y 4/2009
(Continued)

OTHER PUBLICATIONS

Office Action of Japanese Application No. 2020-003171 corresponding to co-pending U.S. Appl. No. 15/897,086—4 pages (dated Apr. 7, 2020).

(Continued)

*Primary Examiner* — Thomas McEvoy
(74) *Attorney, Agent, or Firm* — K&L Gates LLP

(57) ABSTRACT

A surgical procedure kit for inserting a medical tube according to the present invention includes: an insertion pathway formation means configured to include a medical tube provided with a hollow tube main body, a tube member including a hollow conduit having the medical tube received therein and forming a pathway into which the medical tube is to be inserted, and a support member including a support rod which is inserted into the medical tube and has stiffness greater than that of the tube member; and a push means configured to be slidable within the conduit of the tube member and push the medical tube through the conduit of the tube member.

15 Claims, 7 Drawing Sheets

(51) Int. Cl.
   *A61B 17/00* (2006.01)
   *A61B 17/06* (2006.01)
(52) U.S. Cl.
   CPC .............. *A61B 2017/06176* (2013.01); *A61B 2017/06185* (2013.01)

(56) References Cited

U.S. PATENT DOCUMENTS

| | | | |
|---|---|---|---|
| 4,744,364 A | 5/1988 | Kensey | |
| 4,805,292 A | 2/1989 | Noguchi | |
| 4,844,364 A | 7/1989 | Rossouw | |
| 4,922,904 A | 5/1990 | Uetake | |
| 4,932,962 A | 6/1990 | Yoon et al. | |
| 5,041,129 A | 8/1991 | Hayhurst et al. | |
| 5,053,046 A | 10/1991 | Janese | |
| 5,053,047 A | 10/1991 | Yoon | |
| 5,080,667 A | 4/1992 | Chen et al. | |
| 5,192,301 A | 3/1993 | Kamiya et al. | |
| 5,207,694 A | 5/1993 | Broome | |
| 5,224,955 A | 7/1993 | West | |
| 5,236,443 A | 8/1993 | Sontag | |
| 5,259,846 A | 11/1993 | Granger et al. | |
| 5,269,809 A | 12/1993 | Hayhurst et al. | |
| 5,306,294 A | 4/1994 | Winston et al. | |
| 5,330,503 A | 7/1994 | Yoon | |
| 5,500,000 A | 3/1996 | Feagin | |
| 5,626,614 A | 5/1997 | Hart | |
| 5,643,295 A | 7/1997 | Yoon | |
| 5,683,417 A | 11/1997 | Cooper | |
| 5,741,299 A | 4/1998 | Rudt | |
| 5,931,855 A | 8/1999 | Buncke et al. | |
| 6,241,747 B1 | 6/2001 | Ruff | |
| 6,390,993 B1 * | 5/2002 | Cornish ................ A61M 25/09 600/585 |
| 6,939,326 B1 | 9/2005 | Thappa | |
| 7,056,331 B2 | 6/2006 | Kaplan et al. | |
| 7,468,068 B2 | 12/2008 | Kolster | |
| 7,582,105 B2 | 9/2009 | Kolster | |
| 7,601,164 B2 | 10/2009 | Wu | |
| 7,967,841 B2 | 6/2011 | Yuan et al. | |
| 7,988,727 B2 | 8/2011 | Santamore et al. | |
| 8,192,462 B2 | 6/2012 | Sulamanidze et al. | |
| 8,747,438 B2 | 6/2014 | Longo et al. | |
| 8,758,367 B2 | 6/2014 | Philippon et al. | |
| 9,044,224 B2 | 6/2015 | Lauria | |
| 9,125,647 B2 | 9/2015 | Goraltchouk et al. | |
| 9,204,965 B2 | 12/2015 | Longoria | |
| 9,675,341 B2 | 6/2017 | D'agostino et al. | |
| 9,808,234 B2 | 11/2017 | Kim | |
| 9,848,865 B2 | 12/2017 | Kim | |
| 9,924,937 B2 | 3/2018 | Kim | |
| 10,010,317 B2 | 7/2018 | Kim | |
| 10,178,990 B2 | 1/2019 | Kim | |
| 10,226,320 B2 | 3/2019 | Kim | |
| 2002/0198544 A1 | 12/2002 | Uflacker | |
| 2003/0149447 A1 | 8/2003 | Morency et al. | |
| 2004/0030319 A1 | 2/2004 | Korkor et al. | |
| 2004/0030354 A1 | 2/2004 | Leung et al. | |
| 2004/0153102 A1 | 8/2004 | Therin et al. | |
| 2005/0101984 A1 | 5/2005 | Chanduszko et al. | |
| 2005/0240224 A1 | 10/2005 | Wu | |
| 2005/0245963 A1 | 11/2005 | Kida et al. | |
| 2006/0079935 A1 | 4/2006 | Kolster | |
| 2006/0135994 A1 | 6/2006 | Ruff et al. | |
| 2006/0135996 A1 | 6/2006 | Schwartz et al. | |
| 2006/0265010 A1 | 11/2006 | Paraschac et al. | |
| 2007/0038249 A1 | 2/2007 | Kolster | |
| 2007/0049971 A1 | 3/2007 | Chin et al. | |
| 2007/0167958 A1 | 7/2007 | Sulamanidze et al. | |
| 2007/0213770 A1 | 9/2007 | Dreyfuss | |
| 2008/0058816 A1 | 3/2008 | Philippon et al. | |
| 2008/0132943 A1 | 6/2008 | Maiorino et al. | |
| 2008/0228144 A1 | 9/2008 | Liniger et al. | |
| 2008/0281357 A1 | 11/2008 | Sung et al. | |
| 2009/0088797 A1 | 4/2009 | Crombie et al. | |
| 2009/0093670 A1 | 4/2009 | Annest et al. | |
| 2009/0112259 A1 | 4/2009 | D'Agostino | |
| 2009/0210003 A1 | 8/2009 | Sulamanidze et al. | |
| 2009/0299407 A1 | 12/2009 | Yuan et al. | |
| 2010/0137679 A1 | 6/2010 | Lashinski et al. | |
| 2010/0160961 A1 | 6/2010 | Nawrocki et al. | |
| 2011/0054522 A1 | 3/2011 | Lindh et al. | |
| 2011/0238111 A1 | 9/2011 | Frank | |
| 2011/0270304 A1 | 11/2011 | Lee | |
| 2011/0276090 A1 | 11/2011 | Berndt et al. | |
| 2011/0282386 A1 | 11/2011 | Friedrich et al. | |
| 2011/0288563 A1 | 11/2011 | Gianotti et al. | |
| 2012/0109193 A1 | 5/2012 | Primavera et al. | |
| 2012/0109195 A1 | 5/2012 | Odermatt et al. | |
| 2012/0239002 A1 | 9/2012 | Griswold | |
| 2012/0316632 A1 * | 12/2012 | Gao .................. A61F 2/86 623/1.2 |
| 2013/0245684 A1 | 9/2013 | Ruff et al. | |
| 2013/0345745 A1 | 12/2013 | Kim | |
| 2014/0155913 A1 | 6/2014 | Kim | |
| 2014/0228971 A1 | 8/2014 | Kim | |
| 2014/0364904 A1 | 12/2014 | Kim | |
| 2015/0119985 A1 * | 4/2015 | Lee ................ A61B 17/06166 623/15.12 |
| 2015/0305736 A1 | 10/2015 | Kim | |
| 2015/0366553 A1 | 12/2015 | Kim | |
| 2016/0242899 A1 | 8/2016 | Lee et al. | |
| 2016/0302905 A1 | 10/2016 | Kim | |
| 2018/0116648 A1 | 5/2018 | Kim | |
| 2018/0168567 A1 | 6/2018 | Kim | |
| 2018/0303477 A1 | 10/2018 | Kim | |

FOREIGN PATENT DOCUMENTS

| | | |
|---|---|---|
| CN | 101500495 A | 8/2009 |
| CN | 201692490 U | 1/2011 |
| CN | 102271734 A | 12/2011 |
| DE | 3223153 C1 | 8/1983 |
| DE | 102008057213 A1 | 5/2010 |
| EP | 0314412 A1 | 5/1989 |
| EP | 1929961 A2 | 6/2008 |
| EP | 1955720 A1 | 8/2008 |
| EP | 2020209 A1 | 2/2009 |
| EP | 2108316 A2 | 10/2009 |
| EP | 2386252 A1 | 11/2011 |
| EP | 2386323 A2 | 11/2011 |
| GB | 1091282 A | 11/1967 |
| JP | 2-45703 U | 3/1990 |
| JP | 04-250151 A | 9/1992 |
| JP | 04-307050 A | 10/1992 |
| JP | 04-307052 A | 10/1992 |
| JP | 08-52154 A | 2/1996 |
| JP | 08-140982 A | 6/1996 |
| JP | 02-277459 B2 | 5/1998 |
| JP | 10-258123 A | 9/1998 |
| JP | 10-272182 A | 10/1998 |
| JP | 2000-202029 A | 7/2000 |
| JP | 3069906 U | 7/2000 |
| JP | 2000-225118 A | 8/2000 |
| JP | 2000-232984 A | 8/2000 |
| JP | 2002-516585 A | 6/2002 |
| JP | 2003-019683 A | 1/2003 |
| JP | 2004-041492 A | 2/2004 |
| JP | 2004-057516 A | 2/2004 |
| JP | 2004-073403 A | 3/2004 |
| JP | 2004-121634 A | 4/2004 |
| JP | 2004-530524 A | 10/2004 |
| JP | 2004-329964 A | 11/2004 |
| JP | 2005-177499 A | 7/2005 |
| JP | 2005-177500 A | 7/2005 |
| JP | 2006-025867 A | 2/2006 |
| JP | 2006-515203 A | 5/2006 |
| JP | 2006-516902 | 7/2006 |
| JP | 2007-075616 A | 3/2007 |
| JP | 2007-090062 A | 4/2007 |
| JP | 2007-522837 A | 8/2007 |
| JP | 2007-537017 A | 12/2007 |
| JP | 2008-114074 A | 5/2008 |
| JP | 2008-514382 A | 5/2008 |

(56) References Cited

FOREIGN PATENT DOCUMENTS

| | | |
|---|---|---|
| JP | 2008-132327 A | 6/2008 |
| JP | 2008-132328 A | 6/2008 |
| JP | 2008-132329 A | 6/2008 |
| JP | 2008-546454 A | 12/2008 |
| JP | 2009-517156 A | 4/2009 |
| JP | 2009-531071 A | 9/2009 |
| JP | 2009-247890 A | 10/2009 |
| JP | 2009-279393 A | 12/2009 |
| JP | 2010-500102 A | 1/2010 |
| JP | 2010-507453 A | 3/2010 |
| JP | 2010-518902 A | 6/2010 |
| JP | 2010-537676 A | 12/2010 |
| JP | 2011-500208 A | 1/2011 |
| JP | 2011-240133 A | 12/2011 |
| JP | 2011-240134 A | 12/2011 |
| JP | 2012-515015 A | 7/2012 |
| JP | 2014-514017 A | 6/2014 |
| JP | 6410980 B2 | 10/2018 |
| KR | 10-0178358 B1 | 4/1998 |
| KR | 20-0287634 Y1 | 8/2002 |
| KR | 20-0320005 Y1 | 7/2003 |
| KR | 10-0473108 B1 | 3/2005 |
| KR | 10-2005-0108494 A | 11/2005 |
| KR | 10-0761921 B1 | 10/2007 |
| KR | 10-2008-0039345 A | 5/2008 |
| KR | 10-2009-0035692 A | 4/2009 |
| KR | 10-2009-0103639 A | 10/2009 |
| KR | 10-2010-0120642 A | 11/2010 |
| KR | 20-0451570 Y1 | 12/2010 |
| KR | 10-2011-0019895 A | 3/2011 |
| KR | 10-1044731 B1 | 6/2011 |
| KR | 10-1057376 B1 | 8/2011 |
| KR | 10-1105647 B1 | 1/2012 |
| KR | 10-2012-0010049 A | 2/2012 |
| KR | 10-1132841 B1 | 4/2012 |
| KR | 10-1155817 B1 | 6/2012 |
| KR | 10-1182337 B1 | 9/2012 |
| KR | 10-1185583 B1 | 9/2012 |
| KR | 10-1326736 B1 | 11/2013 |
| KR | 10-1326763 B1 | 11/2013 |
| KR | 10-1367902 B1 | 2/2014 |
| KR | 10-1455206 B1 | 10/2014 |
| SU | 700121 A1 | 11/1979 |
| SU | 1178420 A1 | 2/1984 |
| SU | 1360705 A1 | 7/1986 |
| WO | 2006/109377 A1 | 10/2006 |
| WO | 2007/098212 A2 | 8/2007 |
| WO | 2008/020937 A2 | 2/2008 |
| WO | 2008/057261 A1 | 5/2008 |
| WO | 2008/103308 A1 | 8/2008 |
| WO | 2009/027883 A2 | 3/2009 |
| WO | 2009/055105 A1 | 4/2009 |
| WO | 2010/028324 A2 | 3/2010 |
| WO | 2010/052006 A1 | 5/2010 |
| WO | 2010/062743 A | 6/2010 |
| WO | 2010/080014 A2 | 7/2010 |
| WO | 2011/128392 A1 | 10/2011 |
| WO | 2011/139916 A2 | 11/2011 |
| WO | 2012/121538 A2 | 9/2012 |
| WO | 2012/144677 A1 | 10/2012 |
| WO | 2013/169075 A1 | 11/2013 |
| WO | 2015/083864 A1 | 6/2015 |

OTHER PUBLICATIONS

Office Action of Japanese Patent Application No. 2018-178273—4 pages (dated May 14, 2019).
Notice of Reasons for Refusal of Japanese Patent Application No. 2017-132746—4 pages (dated Nov. 6, 2020).
Office Action of corresponding Chinese Patent Application No. 201380082030.5—9 pages (dated Oct. 24, 2018).
Office Action of Japanese Patent Application No. 2016-250538 corresponding to copending U.S. Appl. No. 16/020,769—4 pages (dated Aug. 23, 2018).
Office Action of Japanese Patent Application No. 2018-091563 corresponding to the related application, U.S. Appl. No. 15/853,634—6 pages (dated Jul. 24, 2018).
Extended European Search Report and Written Opinion of corresponding Patent Application No. 13898725.0—9 pages (dated May 24, 2017).
Office Action of Japanese Patent Application No. 2014-207825 corresponding to related U.S. Appl. No. 14/003,390—2pages (dated Jun. 30, 2016).
U.S. Appl. No. 15/102,240.
Karam et al., "Curved Stylet Core Biopsy Results in Larger Cores", American Journal of Roentgenology, vol. 195—3 pages (Jul. 2010).
BD Product Catalog, Jan. 2010, BD Medical.
"Optinova ICM (TM) IV-catheter tubing", Optimus Nova—7 pages (2007).
John Jacobs Medical, "Youngs Lift"—57 pages (Jun. 7, 2012).
"Catheter", retrieved from http://ko.wikipedia.org/wiki/%EC%B9%ED%85%8c%ed%84%B07oldid=13222103—3 pages (Jan. 13, 2015).
"I.V. Catheter, Product Introduction", http://ww.dukwooco.co.kr/english/product/pro_1.htm, Dukwoo Medical Co., Ltd.,—2 pages (Apr. 9, 2016).
Prado et al., "Supplemental Fixation after Endoscopic Brow Elevation using a Single Nylon Suture", QMP's Plastic Surgery Pulse News, vol. 2, No. 1, Quality Medical Publishing, http://www.plasticsurgerypulsenews.com/2/article_dtl.php?QnCategoryID=18QnArticleID=45 (2010).
"Polydioxanone Suture", Metro Korea, retrieved from http://www.metrokr.com/shop/goods/goods_view.php?goodsno=186785506&category=004 (Oct. 30, 2015).
"Safelock Catheter", Lkmedical Co., Ltd. Product Catalog, retrieved from http://www.lkmedical.com (Oct. 30, 2015).
"Qosina, Thousands of Stock Components", Qosina Product Catalog (2014).
"Angiocatheter", retrieved from http://medical-dictionary.thefreedictionary.com/angiocatheter (Oct. 2, 2015).
"Food and drug safety-wife medical equipment e-petitions". Ministry of Food and Drug Safely, retrieved from https://ww.emed.mfds.go kr/ (Nov. 3, 2015).
Office Communication Japanese Patent Office on third party submission of references in Japanese Patent Application No. 2014-549981 (dated Jan. 25, 2016).
Photos of BD Inc's Product, produced on Jul. 18, 2016.
"MediFirst Homepage", http://www.medifirst.co.kr (Nov. 5, 2013).
Office Action of Japanese Patent Application No. 2018-197450 corresponding to co-pending U.S. Appl. No. 15/853,634—3 pages (dated Nov. 6, 2018).
International Search Report dated Sep. 1, 2014 of PCT/KR2013/011310 which is the parent application of U.S. Appl. No. 15/102,240 and its English translation—4 pages.

* cited by examiner

APPARATUS FOR INSERTING MEDICAL TUBE AND SURGICAL PROCEDURE KIT FOR INSERTING MEDICAL TUBE, HAVING SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present invention relates to an apparatus for inserting a medical tube used to do a surgical procedure of inserting the medical tube used for a surgical operation into a body and fixing it, and a surgical procedure kit for inserting a medical tube having the same.

BACKGROUND ART

For connection or suture of a damaged muscle, blood vessel, nerve, and tissue or scars or surgical cutting portions, a medical thread has been used for a long time. Further, the medical thread has also been used for a double eyelid operation, or a surgical procedure, or the like, for removing laxity of tissues or skin, wrinkles, or the like caused due to aging, a reduction in skin elasticity, an external injury, an overdose, a necrosis, or the like. A lifting surgical procedure using the medical thread which lifts a sagging skin and tissue of a face, a chin, a neck, an abdomen, a vagina, a chest, a hip, or the like and pulls and smoothes creases using a needle and a thread without using a knife need not excessively cut a skin and may minimize a generation of scars and reduce bleeding or swelling due to an operation, and therefore has been spotlighted.

However, in the conventional lifting surgical procedure using a medical thread, one insertion puncture hole is formed at a point of a body into which the medical thread is inserted to insert the medical thread into the body and fix it, and at least one fastening puncture hole is formed at a point of the body where the medical thread is fixed, and then the medical thread is inserted through the insertion puncture hole, pushed from behind using rigidity of the medical thread to make a front end of the medical thread protrude through the fastening puncture hole and be expelled out of the body, and thereafter the front end is tied to form a knot, and then again stitches around the knot or cover it with a portion of a skin cut from other body part.

However, such lifting surgical procedure in which passing the medical thread through both of the puncture holes for inserting and expelling the medical thread through the skin and fixing it has a problem in that a plurality of puncture holes need to be formed in the skin, it is not easy to perform an operation of inserting the medical thread into the body, it takes much time to do the lifting surgical procedure, and a risk of the surgical procedure may be increased because an anesthetic level for a patient needs to be high.

Further, the medical thread itself has insufficient stiffness and an insufficient force to maintain its own shape, and therefore has trouble in moving forward while being inserted into the body.

The disclosure of this section is to provide background of the invention. Applicant notes that this section may contain information available before this application. However, by providing this section, Applicant does not admit that any information contained in this section constitutes prior art.

SUMMARY

A basic object of the present invention is to solve the problem of the prior art as described above. More specifically, an object of the present invention is to simplify a surgical procedure of inserting a medical tube having its own stiffness into a biological tissue, do the surgical procedure while making physical wounds of a body small if possible, reduce total time required to do an insertion operation of the medical tube, and insert the medical tube into a predetermined position and firmly fix it.

Another object of the present invention is to provide a surgical procedure apparatus used for a lifting surgical procedure and a procedure kit for the surgical procedure apparatus capable of lifting a sagging skin and tissue of a body and removing wrinkles by inserting the medical tube into a biological tissue.

According to an exemplary embodiment of the present invention, there is provided an apparatus for inserting a medical tube including an insertion pathway formation means, in which the insertion pathway formation means includes: the medical tube provided with a hollow tube main body; a tube member including a hollow conduit having the medical tube received therein and forming a pathway into which the medical tube is to be inserted; and a support member which includes a support rod inserted into the medical tube and having stiffness greater than that of the tube member.

An outer surface of one end of the tube member may be provided with an inclined insertion portion tapered.

An end of the inclined insertion portion may be provided with a second-stage inclined portion tapered at an angle greater than that of the inclined insertion portion.

The inclined insertion portion may be further provided with at least one cutting line which is formed in parallel with an axis direction of the tube member to branch the one end of the tube member.

An outer surface of an end of the medical tube may be provided with a medical tube support to fix the medical tube within a biological tissue.

The medical tube support may be provided with a barb protruding to be inclined toward an end in an opposite direction to an insertion direction of the medical tube.

The medical tube support may have a truncated cone shape having a diameter increasing from an end in an insertion direction of the medical tube toward an end of an opposite side.

In the medical tube, an outer diameter of an end in an insertion direction of the medical tube may be greater than an outer diameter of an end of an opposite side.

The medical tube may be further provided with a barb protruding to be inclined toward an end in an insertion direction of the medical tube.

An inner diameter of the medical tube may be formed to be greater than an outer diameter of the support rod of the support member and an outer diameter of the medical tube may be formed to be smaller than an inner diameter of the conduit of the tube member.

According to another exemplary embodiment of the present invention, there is provided a surgical procedure kit for inserting a medical tube, including: an insertion pathway formation means configured to include a medical tube provided with a hollow tube main body, a tube member including a hollow conduit having the medical tube received therein and forming a pathway into which the medical tube is to be inserted, and a support member which includes a support rod inserted into the medical tube and having stiffness greater than that of the tube member; and a push means configured to be slidable within the conduit of the tube member and push the medical tube through the conduit of the tube member.

The insertion pathway formation means may further include a piercing means forming a boring hole inserted which is to be inserted into a biological tissue.

The push means may include a push rod having a length enough to protrude by penetrating through the insertion pathway formation means.

As described above, the apparatus for inserting a medical tube and the surgical procedure kit for inserting a medical tube having the same according to the embodiments of the present invention may achieve the following effects.

First, the support for fixing the medical tube to the biological tissue is formed in the medical tube, and as a result only single piercing for inserting one end of the medical tube into the biological tissue is formed in the biological tissue, thereby reducing the damage of the biological tissue.

Second, the medical tube may be just inserted into single piercing to complete the surgical procedure for preventing the creases of the skin, thereby simplifying the surgical procedure.

Third, the end of the insertion pathway formation means for inserting the medical tube into the boring hole may be tapered to facilitate the entry into the biological tissue while passing the medical tube therethrough, thereby reducing the friction during the entry into the biological tissue.

Fourth, the tube member of the insertion pathway formation means into which the medical tube is inserted may have flexibility and thus have trouble in moving within the biological skin tissue, but the insertion pathway formation means moves forward within the biological tissue in the state in which the support member having stiffness greater than that of the tube member is inserted into the tube member, thereby easily forming the desired insertion pathway.

Fifth, the inclined insertion portion in which the end of the insertion pathway formation means is tapered may be provided with the second-stage inclined portion again tapered at an angle greater than that to further reduce the entry frictional force of the insertion pathway formation means, thereby facilitating the surgical procedure.

Sixth, the end of the inclined tube insertion portion may be provided with the cutting line to easily expel the medical tube through the inclined tube insertion portion in which the support for supporting the medical tube at a predetermined point within the tissue is formed.

Seventh, the separate push means for making the medical tube enter the biological tissue may be provided to more effectively move the medical tube within the body forward than pushing the medical tube into the biological tissue with the operator's hand.

Eighth, the insertion surgical procedure of the medical tube may be facilitated to reduce the total time required to do the medical tube insertion surgical procedure.

Ninth, the medical tube may be inserted into the predetermined position of the biological tissue to be firmly fixed.

Tenth, the medical tube for pulling the tissue may be inserted into the body to lift the sagging skin and tissue of the body and remove the creases.

Eleventh, as the medical tube has its own stiffness, it is easy to push the medical tube with the push means.

DETAILED DESCRIPTION OF EMBODIMENTS

Figure 1:
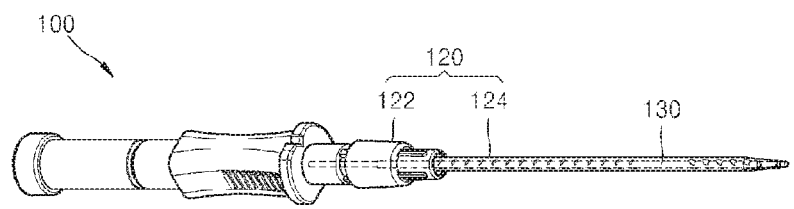
FIG. 1 is an assembled perspective view of a medical tube insertion pathway formation means of an apparatus for inserting a medical tube according to the present invention.

Hereinafter, embodiments of the present invention will be described in detail with reference to the accompanying drawings. To facilitate understanding, certain portions of embodiments of the present invention illustrated in the drawings may be enlarged. Therefore, a proportion between sizes of components is not necessarily limited to one illustrated in the drawings of the present invention.

A surgical procedure kit for inserting a medical tube according to an embodiment of the present invention includes an insertion pathway formation means having the medical tube included therein and forming an entry pathway of the medical tube, and a push means which slides within the insertion pathway formation means to push the medical tube from behind, and if necessary, also includes a piercing means for forming a piercing into a biological skin tissue into which the medical tube is to be inserted.

Figure 2:
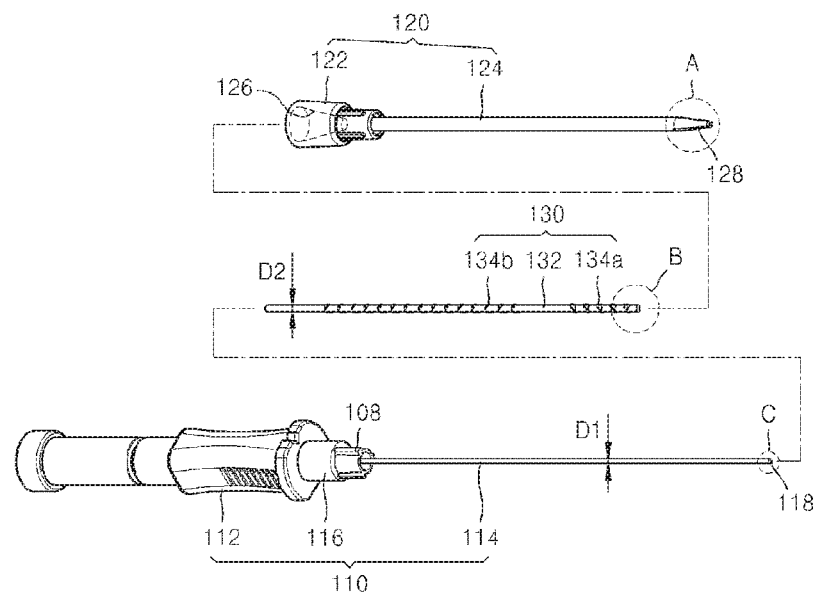
FIG. 2 is an exploded perspective view of the medical tube insertion pathway formation means of the apparatus for inserting a medical tube according to the present invention.

FIG. 1 is an assembled perspective view of an insertion pathway formation means 100 of an apparatus for inserting a medical tube according to the present invention and FIG. 2 is an exploded perspective view of the insertion pathway formation means of FIG. 1.

Referring to FIGS. 1 and 2, the apparatus for inserting a medical tube according to an embodiment of the present invention includes an insertion pathway formation means 100 configured to include a tube member 120 which includes a hollow conduit 124 forming a pathway into which the medical tube is to be inserted, a medical tube 130 which is inserted into the tube member 120 and has a hollow tube main body 132 and has a long pipe shape, and a support member 110 which includes a support rod 114 inserted into the medical tube 130 and having stiffness greater than that of the tube member 120.

The tube member 120 of the insertion pathway formation means 100 moves forward within a biological skin tissue, and therefore is made of an elastic material having predetermined flexibility to prevent the tissue from being damaged. For example, the conduit 124 of the tube member 120 may be made of a silicon material.

The medical tube 130 is made of a material which has a desired stiffness and at the same time flexibility.

The medical tube 130 includes a support of the medical tube 130 formed on an outer surface of one end of the tube main body 132 which has a hollow formed therein and the long pipe shape. When the medical tube is inserted into a body, the support serves to anchor the medical tube at a predetermined position and support a tissue in a body.

The support member 110 of the insertion pathway formation member 100 is inserted into the medical tube 130 inserted into the tube member 120 to solve a problem that the tube member 120 has flexibility and therefore has trouble in moving forward within the biological skin tissue by providing a required level of stiffness to the tube member 120.

Further, the support member 110 includes the support rod 114 long extending from a support fixture 116 which is formed longitudinally from a handle 112 of the support member gripped by an operator and a portion of the support rod 114 opposite to the handle 112 is formed with a tip portion 118 of the support rod.

In FIGS. 1 and 2, a right direction indicates a advancing direction within a biological tissue, that is, a direction toward the inside of a body.

Meanwhile, the medical tube 130 can be slidably inserted into the conduit 124 of the tube member 120 while being supported thereby, and then the support rod 114 of the support member 110 can be slidably inserted into the tube main body 132 of the medical tube 130. The support rod 114 of the support member 110 can be separated from the medical tube 130 in the conduit 124 of the tube member 120 by allowing the operator to pull the handle 112 backward (left direction of the drawing).

Inner diameters and outer diameters of the conduit 124 of the tube member 120, the medical tube 130, and the support rod 114 of the support member 110 can be determined in consideration of a receiving relationship among them. The medical tube 130 needs to be formed at a size enough to be slid within the conduit 124 of the tube member 120 even in the state in which the supports formed on the outer surface thereof protrude and the outer diameter of the support rod 114 of the support member 110 is formed to be smaller than the inner diameter of the tube main body 132 to be slid within the tube main body 132 of the medical tube 130.

The tube member 120 has a fastening portion 122 including a mounting hole 126 into which the support fixture 116 formed at the handle 112 of the support member 110 is inserted. A diameter of a hollow of the mounting hole varies such that an inner surface of the mounting hole 126 is tapered to form an inclined surface. Therefore, as illustrated in FIG. 1, the tip portion 118 of the support member 110 passes through a mounting groove 126 of the tube member 120 in the state in which it penetrates through the tube main body 132 of the medical tube 130 to be disposed inside the conduit 124, and therefore the tip portion 118 is disposed at a position where it does not penetrate through an inclined insertion portion 128 of the tube member 120.

The tip portion 118 of the support member 110 substantially extends up to the inclined insertion portion 128 of the tube member 120 in the state in which the support member 110 penetrates through the medical tube 130 and then is completely inserted into the tube member 120 along with the medical tube 130 to thereby support the inclined insertion portion 128.

FIGS. 3A to 3E are enlarged views of various examples of the inclined insertion portion 128 of the end of the tube member pointing in the advancing direction when the tube member 120 penetrates through the biological tissue.

Referring to FIGS. 3A to 3E, the inclined insertion portion 128 is formed to be tapered at one end of the conduit 124 of the tube member 120 and the end of the inclined insertion portion 128 is provided with a second-stage inclined portion 129 tapered to be inclined at an angle greater than that of the inclined insertion portion 128.

A center of the second-stage inclined portion 129 is provided with a hollow outlet 127, through which the medical tube 130 is expelled. An inner diameter D3 of the hollow outlet 127 has a size enough to allow the medical tube 130 to pass therethrough, and the medical tube may be formed with an outer diameter equal to or greater than the inner diameter D3, such that the medical tube 130 does not pass through the outlet 127 in a loose state but passes through the outlet 127 while elastically expanding the inner diameter D3.

Figure 3A:
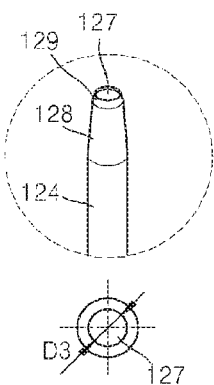
FIGS. 3A to 3E are enlarged views of various examples of part A of FIG. 2.
Figure 3B:
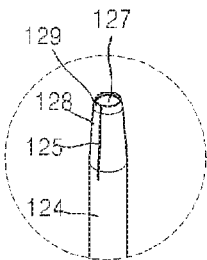
Figure 3B:
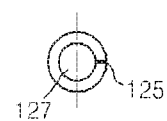

In FIG. 3A, the inclined insertion portion 128 is not provided with a cutting line at all so that the medical tube 130 passes through the outlet 127 while elastically expanding the outlet 127. However, in FIG. 3B, the inclined insertion portion 128 is provided with one cutting line 125 parallel with a longitudinal direction. Therefore, when the medical tube 130 exits through the outlet 127, the inclined insertion portion 128 can be bent from the cutting line 125, and as a result the medical tube assembly can be expelled easily through the outlet 127.

Figure 3C:
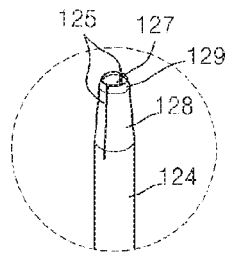
Figure 3C:
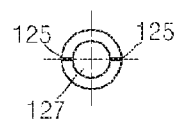
Figure 3D:
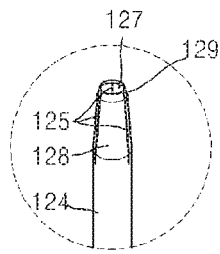
Figure 3D:
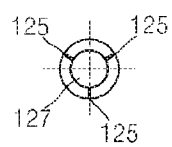
Figure 3E:
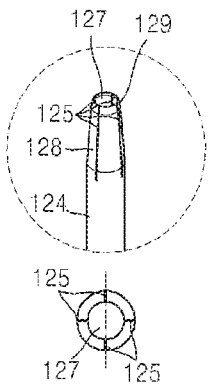

FIG. 3C illustrates an example in which two cutting lines 125 are formed, facing each other with respect to the outlet 127, FIG. 3D illustrates an example in which three cutting lines 125 are formed at an interval of 120° around the outlet 127, and FIG. 3E illustrates an example in which four cutting lines 125 are formed at an interval of 90° therebetween around the outlet 127.

Figure 4:
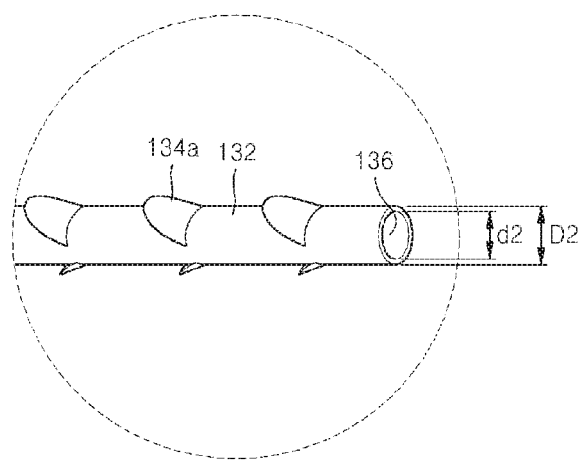
FIG. 4 is a partial enlarged view of part B of FIG. 2.
Figure 5:
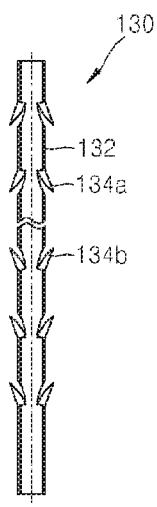
FIG. 5 is an enlarged view of the medical tube of FIG. 2 as a whole.

FIG. 4 is a partial enlarged view of part B of FIG. 2, and FIG. 5 is an enlarged view of the medical tube of FIG. 2 as a whole. Referring to FIGS. 4 and 5, the outer surface of one end of the tube main body 132 having a predetermined inner diameter D2 is provided with a support for anchoring the tube at a predetermined position in a body when the medical tube 130 is inserted into the body and the support may be a first barb 134a protruding to have single directivity on the outer surface of the tube main body 132.

The first barb 134a is formed at an end portion pointing in an insertion direction of the medical tube 130 and protrudes to be inclined toward an end portion pointing in an opposite direction to the insertion direction.

Meanwhile, as illustrated in FIGS. 2 and 5, the end in the opposite direction to the insertion direction of the medical tube 130 is also formed with a second barb 134b protruding to be inclined in an opposite direction to the first barb 134a. When the medical tube 130 is inserted into the body, the second barb 134b gives directivity to lift the tissue in one direction.

Figure 6A:
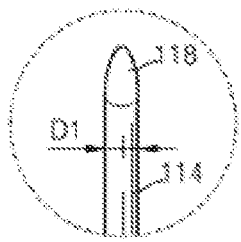
FIGS. 6A and 6B are enlarged views of various examples of part C of FIG. 2.
Figure 6B:
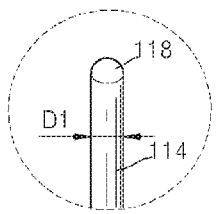

FIGS. 6A and 6B are enlarged views of two examples of part C of FIG. 2.

Referring to FIG. 6A, the tip portion 118 of the support rod 114 of the support member 110 may have a side cross section of a partial shape of an oval and referring to FIG. 6B, the tip portion 118 of the support rod 114 of the support member 110 may have a side cross section having a partial shape of a circle. The support rod 114 is assembled in the state in which it penetrates through the tube main body 132 of the medical tube 130 and then is inserted into the conduit 124 of the tube member 120, and therefore the outer diameter of the support rod 114 is formed to be smaller than the inner diameter of the tube main body 132 of the medical tube 130.

Figure 7:
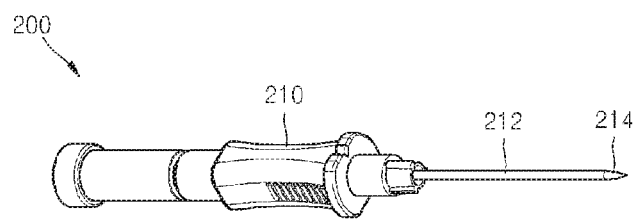
FIG. 7 is a perspective view of a piercing means of a surgical procedure kit for inserting a medical tube having the apparatus for inserting a medical tube according to the present invention.

FIG. 7 is a perspective view of a piercing means 200 which constitutes a part of a surgical procedure kit for inserting a medical tube according to one aspect of the present invention. The piercing means 200 is a means to allow an operator to form a start portion of the insertion pathway formation means 100 and to secure an approximate pathway with respect to a progress pathway within a tissue in which the insertion pathway formation means 100 is to be advanced.

In the piercing means 200, an end of a long boring rod 212 is provided with a sharp piercing portion 214 for forming the boring hole in the skin tissue and an end of the piercing rod 212 opposite to the piercing portion 214 is provided with a handle 210.

Figure 8:
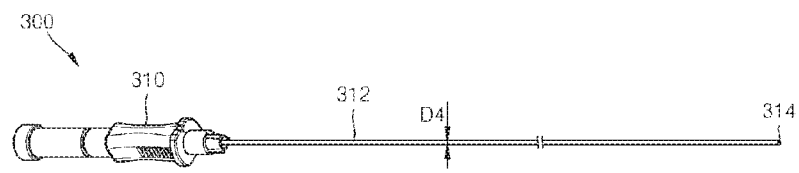
FIG. 8 is a perspective view of a push means of the surgical procedure kit for inserting a medical tube having the apparatus for inserting a medical tube according to the present invention.

FIG. 8 illustrates a perspective view of a push means included in a surgical procedure kit for inserting a medical tube according to one aspect of the present invention. The surgical procedure kit for inserting a medical tube according to one aspect of the present invention includes a push means 300 for pushing the medical tube in a medical tube supply means 400 (FIG. 7A) coupled with the tube member 120 after the support member 110 has been removed from the insertion pathway formation means 100 of FIG. 1.

The push means 300 includes a handle 310 of the push means 300 gripped by the operator, a push rod 312 extending from the handle, and a push portion 314 formed at an end of the push rod 312 to contact and push the medical tube.

The push rod 312 is formed to have a length enough to protrude by penetrating through the medical tube supply means 400 and the insertion pathway formation means 100.

Figure 9:
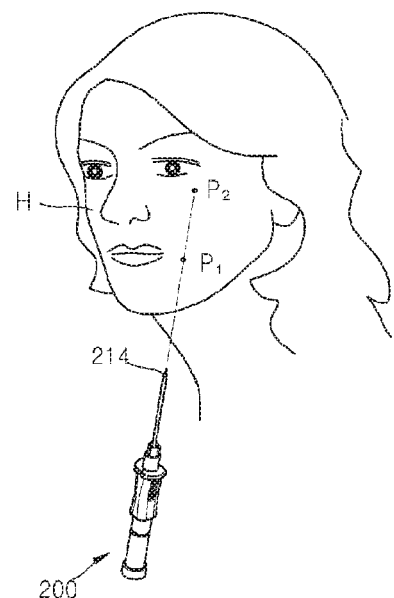
FIG. 9 is a schematic diagram for describing a skin piercing step with the use of the piercing means of the surgical procedure kit for inserting a medical tube having the apparatus for inserting a medical tube according to the present invention.

FIG. 9 exemplarily illustrates an insertion position P1 of the medical tube and a fixed position P2 of the medical tube in a human face, in the apparatus for inserting a medical tube according to the present invention. That is, a piercing is formed by pricking with the use of the piercing means 200 of the surgical procedure kit for inserting a medical tube according to the present invention the position where the medical tube enters a skin tissue, and the medical tube 130 is inserted into the tissue by the insertion pathway formation means 100 inserted through the position P1 and then is fixed to the tissue at the predetermined position P2 by a first barb 134a which is a support.

FIGS. 10A to 10G illustrate a use order of each component of the surgical procedure kit for inserting a medical tube during the surgical procedure of inserting the medical tube into the biological tissue using the surgical procedure kit for inserting a medical tube according to the present invention.

Figure 10A:
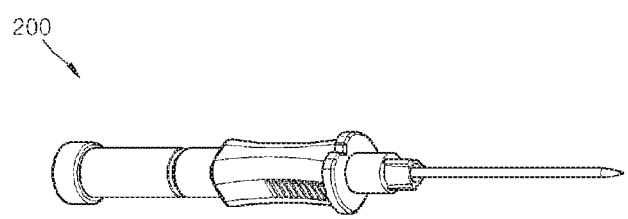
FIGS. 10A to 10G are schematic diagrams for describing a step of performing a lifting surgical procedure with the use of the surgical procedure kit for inserting a medical tube having the apparatus for inserting a medical tube according to the present invention.
Figure 10B:
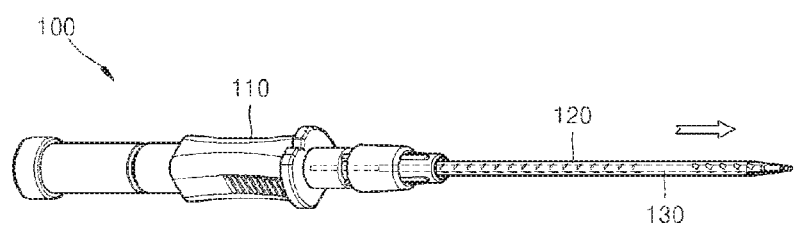

Referring to FIGS. 9 and 10A, the predetermined position P1 of the body is pierced by using the piercing means 200. Next, as illustrated in FIG. 10B, the operator makes the insertion pathway formation means 100 enter the position P1 where the piercing means is extracted. In this case, the insertion pathway formation means 100 is inserted into the biological tissue in the state in which the support member 110 penetrating through the medical tube 130 is assembled in the tube member 120. During this process, the tube member 120 itself has flexibility, and thus the insertion pathway formation means 100 does not easily enter the skin tissue only with the tube member itself, but the support member 110 having stiffness greater than that of the tube member is inserted into the tube member 120 to serve as a frame of the tube member 120, such that the insertion pathway formation means 100 can easily enter up to the predetermined position P2 within the skin tissue.

Figure 10C:
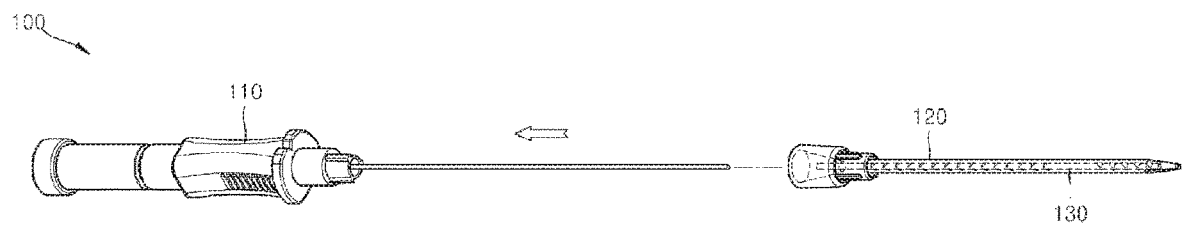

Next, as illustrated in FIG. 10C, if the end of the insertion pathway formation means 100 substantially reaches the position P2 of the skin tissue, the operator pulls back and separates only the support member 110 to extract the support member 110 in the state in which the tube member 120 is inserted into the skin tissue while the medical tube 130 is included in the tube member 120 of the insertion pathway formation means 100.

Figure 10D:
Figure 10E:
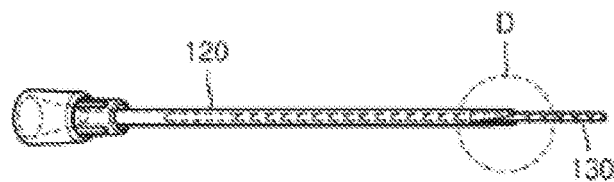
Figure 10F:
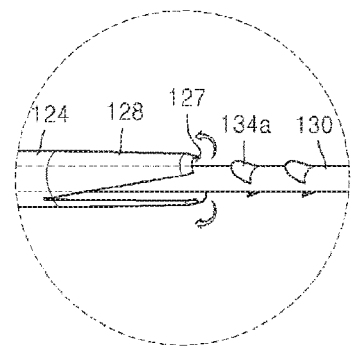

Next, as illustrated in FIG. 10D, the push means 300 is prepared in the state in which the tube member 120 having the medical tube 130 included therein is inserted into the body, and as illustrated in FIGS. 10E and 10F, the operator pushes the medical tube 130 disposed within the tube member 120 from behind using the push means 300.

In this case, if an outer diameter of the push portion of the push means 300 is smaller than the inner diameter of the tube main body 132 of the medical tube 130, when the push means 300 pushes the medical tube 130, the push means 300 is inserted into the tube main body 132 of the medical tube 130, and thus the push means 300 does not push the medical tube 130. To prevent such problem, the outer diameter of the push portion of the push means 300 is formed to be greater than the inner diameter of the tube main body 132 of the medical tube 130. If necessary, the end of the push portion may also be provided with a push plate for pushing the medical tube.

When the operator pushes the medical tube 130 in the tube member 120 using the push means 300, the medical tube 130 is guided within the tube member 120 to be expelled through the outlet 127 of the inclined insertion portion 128 of the end of the tube member 120.

As illustrated in FIG. 10F, when the medical tube 410 is expelled through the inclined insertion portion of the tube member 120, the diameter of the inclined insertion portion 128 is expanded to be bent so that the medical tube 130 can exit easily. For example, as illustrated in FIG. 10F, the inclined insertion portion 128 is expanded with respect to the cutting line formed in the inclined insertion portion 128 and thus its diameter is increased and the tube main body 132 of the medical tube 130 is expelled through the outlet having the increased diameter. In this case, the first barb 134a formed on the outer surface of the tube main body 132 of the medical tube 130 protrudes to be inclined toward the opposite direction to the progress direction of the medical tube, and therefore the interference does not occur when the medical tube 130 is expelled from the conduit 124 of the tube member 120. When the medical tube 130 is extracted from the outlet 127 of the conduit 124, the first barb 134a is folded downward and laid down to a position substantially parallel to an axis direction of the medical tube 130, and after being completely expelled out of the outlet 127, the first barb is again recovered to an original inclined shape by its elasticity.

The operator additionally pushes the push means 300 to accurately adjust the medical tube 130 to the fixed position within the skin tissue. In this process, as the first barb 134a has an inclined shape to have single directivity, the medical tube can be securely anchored after the medical tube 130 is positioned in the tissue in the body.

Figure 10G:
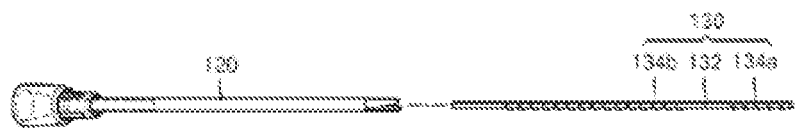

After the medical tube 130 reaches at a predetermined position and is fixed, as illustrated in FIGS. 10E and 10G, both of the push means 300 and the tube member 120 of the insertion pathway formation means are pulled back and extracted. The medical tube 130 is completely expelled out of the inclined insertion portion 128 through this process and thus is disposed within the skin tissue.

As illustrated in FIG. 10G, the first barb 134a which is the support of the medical tube 130 is fixed at the predetermined point of the skin tissue due to the structure in which it protrudes to be inclined toward the opposite direction to the entry direction of the medical tube, and the second barbs 134b formed on the outer surface of the end portion of the opposite side (left direction in the drawing) of the end of the medical tube 410, on which the first barbs 134a are formed serve to pull and fix the skin tissue.

Next, the operator pushes the skin tissue in a predetermined direction in the state in which the medical tube is inserted and fixed, thereby adjusting the pulling direction of the skin tissue.

The medical tube and the support (for example, barb) formed in the medical tube which are used in one embodiment of the present invention may be made of a material which is not absorbed into a body or may be made of even an absorbable material according to the purpose. For example, nylon, polypropylene (for example, MESH, etc.), polyvinyliden fluoride, polyester, stainless steel, gold, titanium, silicon, MedPor, Gore-Tex, mesh, polylactic acid, polydioxanone (PDO, PDS), a copolymer of lactic acid and glycolic acid, or the like may be used but the present invention is not limited thereto. When the material absorbable into the body is used, there is an advantage in that after suture of the inside of the body is performed, the support needs not to be removed.

According to one embodiment of the present invention, the medical tube on which the barbs are formed may have, for example, a circular cross section, but the present invention is not necessarily limited thereto. Therefore, the medical tube may also have a triangular cross section, a quadrangular cross section, or the like, if necessary.

The barb may be arranged on the outer surface of the medical tube depending on the required configuration and may be formed by any appropriate method including ones well known in the technical field of the present invention. The methods may include a knife, a laser, injection molding by press forming, stamping, and cutting. The required number of cutting at an acute angle is performed on the medical tube. A size of the barb may be appropriately adjusted according to the purpose within the scope of the technical field of the present invention. For example, a depth of the barb formed in the medical tube may be about 30 to 100 micron and may be adjusted depending on the diameter of the medical tube. An interval between the barbs formed on the surface of the medical tube may be 100 micron to 1 mm or may be greater than that.

The medical tube used in the present invention may be made of several materials of a polymer material, a metal material, a biological material, or the like and may be made of, for example, a non-absorbable material, such as polypropylene, gold, stainless steel, titanium, nylon, polyvinyliden fluoride, polyester, and braided silk or an absorbable material such as polydioxanone (PDO, PDS), but the present invention is not limited thereto.

EXAMPLES

Figure 11A:
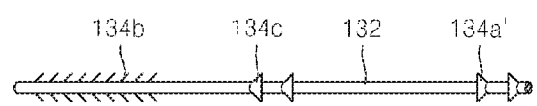
FIGS. 11A to 11C are side views of a medical tube according to another embodiment of the present invention, for use in a surgical procedure kit for inserting a medical tube having an apparatus for inserting a medical tube.
Figure 11B:
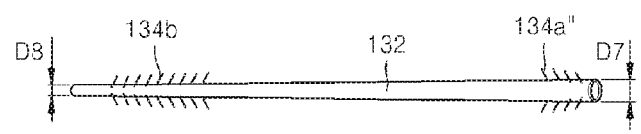
Figure 11C:
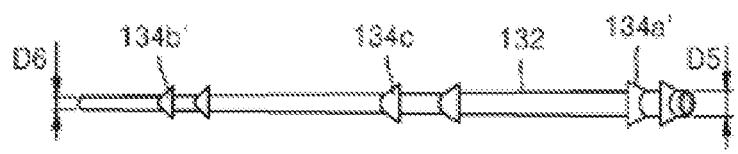

As an alternative of the medical tube 130 according to the embodiment of the present invention as illustrated in FIGS. 4 and 5, the medical tube 130 which includes the tube main body 132 and supports 134a' and 134a'' having various forms exemplarily illustrated in FIGS. 11A to 11C may be used.

Referring to FIG. 11A, the medical tube 130 may have a straight shape and the end in a direction in which the medical tube 130 enters the skin tissue may be provided with at least one support 134a' having a truncated cone structure which has single directivity, the end of the opposite side of the medical tube 130 may be provided with a plurality of barbs 134b protruding to be inclined toward the end (right direction in the drawing) in the insertion direction of the medical tube, and a plurality of fixing portion 134c having the truncated cone structure which has single directivity opposite to the support 134a' may be disposed between the support 134a' and the barb 134b.

As an optional embodiment, referring to FIG. 11B, the medical tube 410 may have a straight form and may be provided with at least one support 134a' having the truncated cone structure which has single directivity and the end of the opposite side of the medical tube 130 may be provided with at least one fixing portion 134b' and 134c having a truncated cone structure which has directivity opposite to the support 134a', instead of the barb of FIG. 11A.

In this case, the medical tube requires a relatively high stiffness in the direction in which the medical tube enters the skin tissue, and therefore to satisfy this, a diameter D5 of the medical tube in a direction in which the medical tube enters the skin tissue may be formed to be greater than a diameter D6 of the medical tube at the end in the opposite direction thereto.

Optionally, as illustrated in FIG. 11C, the barb 134a'' having single directivity may be disposed at both ends of the medical tube instead of the support having the truncated cone structure.

Referring to FIG. 11C, the barb formed at the end in the direction in which the medical tube 130 enters the skin tissue is provided with the first barb 134a'' protruding to be inclined toward an opposite direction to the direction in which the medical tube enters the skin tissue, and the end of the opposite side to the end of the medical tube provided with the first barb 134a'' is provided with the second barb 134b protruding to be inclined in the opposite direction to the first barb 134a''.

In this case, similar to FIG. 11B, the medical tube requires a relatively high stiffness in the direction in which the medical tube enters the skin tissue, and therefore to satisfy this, a diameter D7 of the medical tube in a direction in which the medical tube enters the skin tissue may be formed to be greater than a diameter D8 of the medical tube at the end in the opposite direction thereto.

Although the present invention has been described with reference to exemplary embodiments shown in the accompanying drawings, it is only an example. It will be understood by those skilled in the art that various modifications and equivalent other exemplary embodiments are possible from the present invention. In particular, although the apparatus for inserting a medical tube of the present invention is described for the application of, for example, a lifting surgical procedure (so called face lift surgical procedure) for reducing creases of a facial skin, the protective scope of the present invention is not limited thereto, or rather the apparatus for inserting a medical tube may also be applied to a surgical procedure performing a surgical procedure of lifting the sagging skin or tissue and reducing creases at various parts of a body, including an animal other than a person and may be applied to a medical purpose for forming a pulling force in the biological tissue as another purpose, not for the removal of the creases of the skin. Accordingly, the actual technical protection scope of the present invention must be determined by the technical idea of the appended claims.

The present invention may be used for a medical surgical procedure field.

The invention claimed is:

1. A method of performing a skin lifting surgery, the method comprising:
    providing an insertion unit comprising a hollow pipe, a medical tube and a support rod, in which the medical tube is loaded inside the hollow pipe and the support rod is inserted into both the hollow pipe and the medical tube such that at least part of the support rod is surrounded by both the medical tube and hollow pipe and further such that the insertion unit is elongated between a proximal end and a distal end thereof, wherein the medical tube comprises a tube body and a plurality of barbs projecting from a circumference of the tube body;
    forming a hole into skin of a subject's body;
    inserting the insertion unit through the hole and advancing the insertion unit underneath the skin until the distal end of the insertion unit reaches a target area within the skin, by which the insertion unit extends underneath the skin along an axis extending between the hole and the target area;
    pulling the support rod out of underneath the skin while keeping the hollow pipe underneath the skin extending along the axis and the medical tube staying inside the hollow pipe;
    subsequently, pushing the medical tube to advance toward the target area using a push rod such that the medical tube travels further toward the target area relative to the hollow pipe and such that at least part of the plurality of barbs reaches the target area out of the hollow pipe; and
    subsequently, pulling the hollow pipe out of underneath the skin while maintaining the medical tube underneath the skin extending along the axis extending between the hole and the target area.

2. The method of claim 1, wherein the hollow pipe comprises a distal end portion, wherein the support rod comprise a distal end portion, wherein the hollow pipe is made of a first material and the support rod is made of a second material that is harder than the first material.

3. The method of claim 2, wherein, when the support rod is fully inserted into the hollow pipe, the distal end portion of the support rod reaches the distal end portion of the hollow pipe.

4. The method of claim 2, wherein the distal end portion of the hollow pipe is tapered, wherein, when pushed to advance the medical tube toward the target area, the medical tube comes out of the tapered distal end portion of the hollow tube.

5. The method of claim 1, wherein an end portion of the hollow pipe is tapered.

6. The method of claim 5, wherein the tapered end portion of the hollow pipe comprises at least two different slopes with respect to a longitudinal axis of the hollow pipe.

7. The method of claim 5, wherein the tapered end portion comprises at least one cut line extending along a longitudinal direction of the hollow pipe.

8. The method of claim 1, wherein the medical tube comprises a leading portion, a trailing portion and an intermediate portion between the leading portion and the trailing portion, wherein the plurality of barbs is referred to as a first plurality of barbs, wherein the first plurality of barbs projects from the circumference of the tube body in the leading portion and is inclined toward the trailing portion.

9. The method of claim 8, wherein the medical tube does not comprise barbs in the trailing portion.

10. The method of claim 8, wherein the medical tube further comprises a second plurality of barbs projecting from the circumference of the intermediate portion of the tube body, wherein the second plurality of barbs is inclined toward the leading portion.

11. The method of claim 10, wherein the medical tube further comprises another portion comprising no barbs between the leading portion and the intermediate portion.

12. The method of claim 1, wherein the subject's body comprises the subject's face, wherein the target area is located at a level higher than the hole.

13. The method of claim 12, wherein the insertion unit is inserted along an insertion path that is generally toward an eye of the subject.

14. The method of claim 1, wherein the hole is formed on a cheek of the subject, wherein the insertion unit is inserted along an insertion path that is generally toward an ear of the subject.

15. The method of claim 1, wherein the subject's body comprises the subject's face, wherein the target area is located at a level lower than the hole in the subject's face.

* * * * *